United States Patent [19]

Stadlmann

[11] Patent Number: 4,942,629
[45] Date of Patent: Jul. 24, 1990

[54] SKI GOGGLES WITH HEATED LENS

[75] Inventor: Günter Stadlmann, Linz, Austria

[73] Assignee: Optyl Eyewear Fashion International Corporation, Norwood, N.J.

[21] Appl. No.: 358,704

[22] Filed: May 30, 1989

[30] Foreign Application Priority Data

May 30, 1988 [DE] Fed. Rep. of Germany ....... 3818389

[51] Int. Cl.⁵ ............................ A61F 9/02; H05B 3/26
[52] U.S. Cl. ........................................ 2/435; 2/171.3; 219/211
[58] Field of Search ............... 2/435, 436, 437, 171.3, 2/422, 424, 10, 434, 8, 9; 219/203, 211

[56] References Cited

U.S. PATENT DOCUMENTS

| 4,150,443 | 4/1979 | McNeilly | 2/171.3 X |
| 4,443,893 | 4/1984 | Yamamoto | 2/436 |
| 4,584,721 | 4/1986 | Yamamoto | 2/435 X |
| 4,680,815 | 7/1987 | Hirsch et al. | 2/171.3 |
| 4,682,007 | 7/1987 | Hollander | 2/435 X |

FOREIGN PATENT DOCUMENTS 1605035  10/1972  France ................................. 219/211

Primary Examiner—Peter Nerbun
Attorney, Agent, or Firm—Fitch, Even, Tabin & Flannery

[57] ABSTRACT

Ski goggles are provided having circuitry for heating the lens by means of at least one solar cell held by the headband of the goggles to prevent or eliminate fogging and condensation on the surface of the lens of the goggles facing the wearer.

14 Claims, 2 Drawing Sheets

SKI GOGGLES WITH HEATED LENS

This invention relates to ski goggles with heated lenses for suppressing and eliminating fogging of the lenses when the goggles are being worn.

BACKGROUND OF THE INVENTION

There are already known ski goggles in which the lenses are coated with a layer of a hydrophilic material on the side of the lenses facing the wearer's face. This hydrophilic substance absorbs the moisture from the respiratory air and from transpiration and thus prevents fogging of the lenses. The moisture uptake capacity of such hydrophilic layers, however, is very limited, and these layers generally cannot prevent fogging of the lenses when the ski goggles are worn for long periods of time.

Ski goggles having battery supplies that heat the lenses are definitely superior in effect to goggles with lenses having the hydrophilic coating, but lenses with battery heating require constant maintenance with regard to the operating readiness or the charge of the batteries.

SUMMARY OF THE INVENTION

The problem to which the present invention is directed is to provide ski goggles that have means for creating nonfogging lenses which combines the superior efficacy of battery heated lenses with the lack of maintenance of hydrophilic coated lenses. This problem is solved by providing ski goggles with lenses which, according to this invention, are heated by means of one or more solar cells.

The solar cells are preferably arranged on the headband of the ski goggles and provide the heating current for the lenses as soon as light strikes the cells. If the power consumption of the lenses is minimized and the efficiency of the solar cells is maximized, the amount of light available when skiing will be sufficient to activate the cells and thus heat the lenses.

Preferably, batteries are connected between the solar cells and the lens heating system, the batteries being charged when the solar cells are activated and forming an additional reservoir of current for the lens heating. The solar cells provide an almost permanent supply of power to the batteries and make it possible to quickly eliminate any fogging or condensation on the lenses, if such occurs at all, within a few seconds by simply switching on the lens heating system.

In contrast with the previously known battery heated ski goggles, the ski goggles according to this invention, although they also have batteries, require little or no maintenance with regard to the charge status of the batteries because the batteries are in a charge state during activation of the solar cells.

DESCRIPTION OF THE DRAWINGS

Objects, advantages and features of this invention will become apparent by reference to the accompanying drawings and to the following specification, in which.

DESCRIPTION OF THE INVENTION

Figure 1:
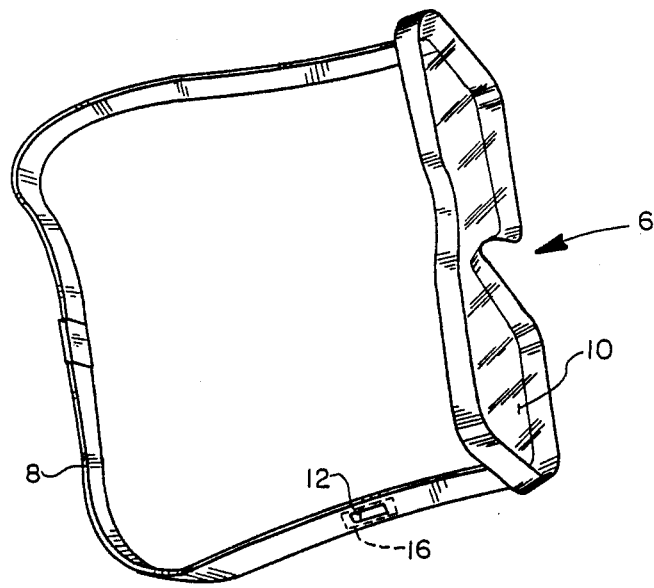
FIG. 1 is a pictorial view of ski goggles embodying this invention.

FIG. 1 shows ski goggles 6 incorporating this invention. The goggles 6 include a headband 8 and a lens 10. The goggles 6 are otherwise typical of goggles that are worn out-of-doors by skiers for protection of their eyes against the elements of weather and various airborne matter that could otherwise be injurious to the eyes while skiing. Heat from the skier's body, of course, generally causes condensation or fogging on the inside surface of the lens facing the skier and disturbs the skier's vision. This problem is overcome by this invention.

Figure 2:
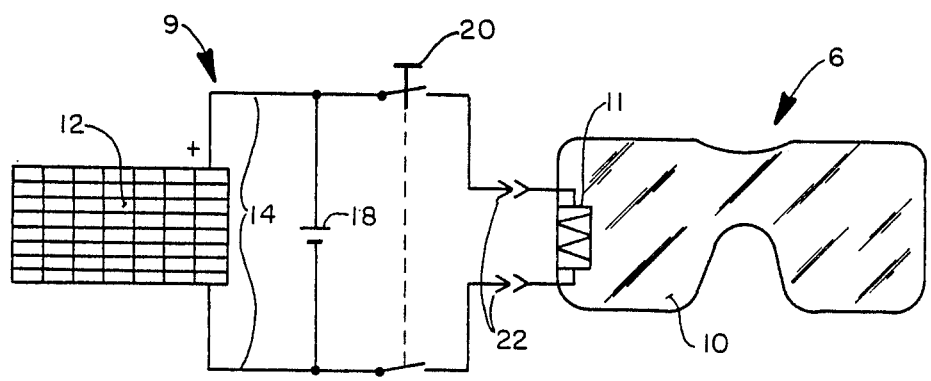
FIG. 2 is a schematic diagram of the invention.
Figure 4:
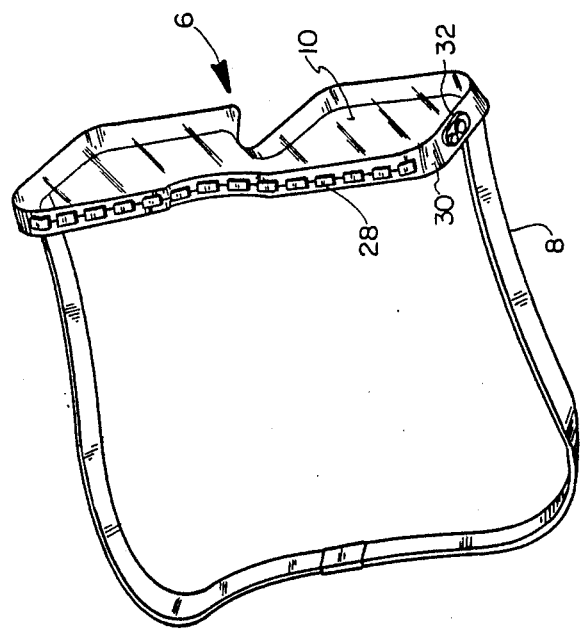
FIG. 4 is a pictorial view of another embodiment of the invention.
Figure 3A:
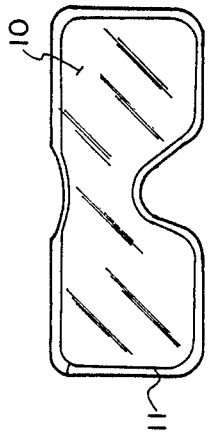
FIG. 3a–3d are pictorial views of a lens in the system constructed in accordance with respective alternative resistive means in accordance with the invention.
Figure 3B:
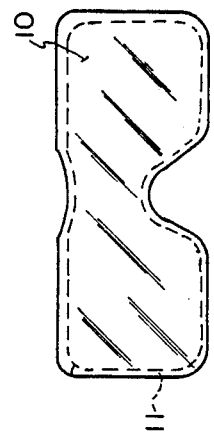
Figure 3C:
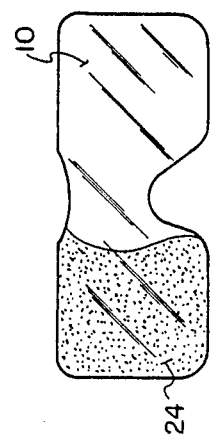
Figure 3D:
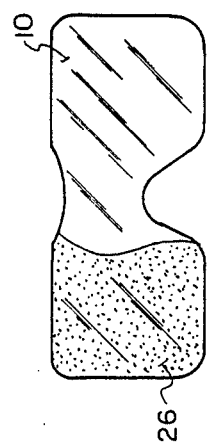

The schematic diagram in FIG. 2 shows one embodiment. In general, there is provided a power supply 9 and a lens heating system 11. The power supply 9 includes a solar cell 12 that provides current to heat the lens 10 by way of wires or lines 14. In general, solar cells furnish important long duration power supplies for satellites and space vehicles as well as for small scale applications. The solar cell is important because when it is exposed to the solar spectrum, it can convert that radiation directly to electricity with high conversion efficiency. Solar cells may consist of a conventional silicon p-n junction, cadmium-sulfide, or many other semiconductors, using various configurations and employing single-crystal, polycrystal, and amorphous thin-film structures. Preferably for this application, the amorphous thin-film structure is used because of its ability to operate while based on a somewhat flexible mounting.

The solar cell 12 is held by, either in or on, the headband 8 of the goggles 6, and it is protected against moisture and mechanical damage by being contained in an envelope 16 of a suitable protective material, such as Tedlar film. Such protective cover can also substantially increase the efficiency of the solar cell 2.

A battery 18 is in constant connection with the solar cell 12, and an on-off switch 20 is provided in the lines 14 between the battery 18 and the lens heating system 11. The heating system 11 of the lens 10 can be switched on and off as needed by means of the switch 20. Instead of the switch 20, special sensors with temperature probes may also be provided, in which case the sensors are actuated manually, semiautomatically or fully automatically according to predetermined temperature parameters, which can be computed in accordance with standard engineering practice.

Since the elimination of fogging and condensation by the lens heating system, supported by ventilation of the goggles which may optionally also be provided, takes place relatively rapidly, the heating system can be switched off again after a short period of operation (up to about 1 minute). In the meantime, the solar cell 12 will charge battery 18 even during skiing to provide "buffered" energy to the system. Thus, the basic requirement, namely to prevent fogging and condensation on the ski goggles even in extreme cases, is satisfied with a system that is relatively maintenance-free.

The lines 14 run from the switch 20 to means such as plug connections 22 provided on the goggles 6 or the lenses 10 to connect and disconnect the lines 14 to the heating system 11. Plug or clamp connections that are easy to handle (not shown) may also be provided on the solar cell 12 and the battery 18 to facilitate assembly of the individual components, so the individual elements of the arrangement, e.g., the lens 10 or the battery 18, can be replaced with relative ease at any time.

The heating system 11 of the lens 10 may consist of a thin heating wire, e.g., a tungsten wire, which is affixed on the surface of the lens or embedded in the material of which the lens is made. When such a thin wire is approximately 20 mm in front on the eye, it is almost not perceived at all by the wearer of the goggles. The heating system 11, however, may also consist of a very thin conductive coating 24 of a transparent dielectric material such as tin oxide, or of a very thin layer of a conductive metallic coating 26 such as a semi-transparent gold or aluminum coating through vacuum metallization which also serves as a sunscreen to partially block intense sunlight from the eyes of the wearer. Wireless on the lens heating by means of infrared diodes 28 mounted on the peripheral edge 30 of the lens 10 can also be effected.

If the ski goggles according to this invention are equipped with a battery that can be constantly recharged by the solar cell, then the battery can also be used to drive a miniature fan 32 such as that known for ski goggles for wearers of corrective lenses to augment the operation of the heating system 11.

An example of ski goggles that has been constructed in accordance with this invention includes a power supply consisting of at least one solar cell that, upon being exposed to sunlight produced a voltage of 1.5 to 2.5 volts and a current of 30 to 60 milliamperes. The battery was a Ni-Fe accumulator having a capacity of 180 mA/h.

Although the invention has been particularly shown and described with reference to preferred embodiments thereof, it will be understood by those skilled in the art that various alterations in form and details may be made therein without departing from the spirit and scope of the invention hereafter claimed.

What is claimed is:

1. Ski goggles with defogging means comprising: a headband, a lens, an electrical resistive means applying heat to the lens when activated, a power supply for electrical connection to the resistive means for activating same, the power supply including at least one solar cell, and at least one battery connected between the solar cell and the lens resistive means as an additional power reservoir for applying heat to the lens.

2. Ski goggles with defogging means comprising: a headband, a lens, an electrical resistive means applying heat to the lens when activated, a power supply for electrical connection to the resistive means for activating same, the power supply including at least one solar cell, the solar cell being held by the headband of the ski goggles, and at least one battery connected between the solar cell and the lens resistive means as an additional power reservoir for applying heat to the lens.

3. Ski goggles according to claim 1 or 2, further comprising switch means provided between the battery and the lens resistive means.

4. Ski goggles according to claim 3, wherein the switch means is an on-off switch.

5. Ski goggles according to claim 3, wherein the switch means is a sensor device having temperature sensors that operate automatically according to preset temperature parameters.

6. Ski goggles according to claim 5, further comprising a manual override means on the sensor device to provide the option of manual, semiautomatic or fully automatic operation.

7. Ski goggles according to claim 1 or 2, wherein the lens resistive means includes a heating wire affixed on the surface of the lens.

8. Ski goggles according to claim 1 or 2, wherein the lens resistive means includes a heating wire embedded in the lens material.

9. Ski goggles according to claim 7, wherein the heating wire is tungsten wire.

10. Ski goggles according to claim 8, wherein the heating wire is tungsten wire.

11. Ski goggles according to claim 1 or 2, wherein the resistive means is a conductive coating applied on the surface of the lens.

12. Ski goggles according to claim 1 or 2, wherein the resistive means is a film of metal applied to the lens by vacuum metallization.

13. Ski goggles according to claim 1 or 2, wherein the resistive means consists of a plurality of infrared diodes mounted on the peripheral edge of the lens.

14. Ski goggles according to claim 1 or 2, further comprising means between the power supply and the lens resistive means for effecting unplugging and disconnecting between the two.

* * * * *